(12) United States Patent
Saxena et al.

(10) Patent No.: US 9,089,505 B1
(45) Date of Patent: Jul. 28, 2015

(54) SKIN FIRMING CREAM

(71) Applicant: Jan Marini Skin Research, San Jose, CA (US)

(72) Inventors: Subhash J. Saxena, Ringoes, NJ (US); Jan L. Marini, San Jose, CA (US)

(73) Assignee: Jan Marini Skin Research, San Jose, CA (US)

( * ) Notice: Subject to any disclaimer, the term of this patent is extended or adjusted under 35 U.S.C. 154(b) by 0 days.

(21) Appl. No.: 14/513,518

(22) Filed: Oct. 14, 2014

(51) Int. Cl.
| | |
|---|---|
| A61K 36/00 | (2006.01) |
| A61K 36/899 | (2006.01) |
| A61K 8/97 | (2006.01) |
| A61K 8/64 | (2006.01) |
| A61K 8/49 | (2006.01) |
| A61K 8/41 | (2006.01) |
| A61K 8/60 | (2006.01) |
| A61K 8/34 | (2006.01) |
| A61K 8/42 | (2006.01) |
| A61Q 19/08 | (2006.01) |

(52) U.S. Cl.
CPC ... *A61K 8/97* (2013.01); *A61K 8/34* (2013.01); *A61K 8/41* (2013.01); *A61K 8/42* (2013.01); *A61K 8/494* (2013.01); *A61K 8/498* (2013.01); *A61K 8/4926* (2013.01); *A61K 8/4953* (2013.01); *A61K 8/60* (2013.01); *A61K 8/64* (2013.01); *A61Q 19/08* (2013.01); *A61K 2800/30* (2013.01)

(58) Field of Classification Search
None
See application file for complete search history.

*Primary Examiner* — Qiuwen Mi
(74) *Attorney, Agent, or Firm* — Bozicevic, Field & Francis LLP; Pamela J. Sherwood

(57) ABSTRACT

The present invention features novel cosmetic skin care compositions for improving the appearance of skin.

20 Claims, No Drawings

SKIN FIRMING CREAM

BACKGROUND OF THE INVENTION

The skin provides the first barrier to the external environment, and as such it is continually subjected to stresses such as extreme heat or cold, attack by microorganisms, exposure to UV radiation, abrasion, chemical irritants and the like. As a result, the skin can show signs of response to damage over time, for example sunburn, roughening, wrinkling, discoloration, and even malignancies, including basal cell carcinoma, squamous cell carcinoma and melanoma. While these effects are often considered to be normal aging, in fact, they are not normal results of aging but are responses to damage.

The delicate neck area is highly susceptible to premature aging because it's thinner than facial skin and has a different collagen content. Plus it is often exposed to the sun, making it particularly vulnerable to ultraviolet light damage. Horizontal creases and deep wrinkles can age the look of the neck. Cosmetic compositions that improve the appearance of skin are provided herein.

SUMMARY OF THE INVENTION

The present invention provides cosmetic formulations for improving the appearance of the skin, including the fine skin of the neck. The cosmetic formulations improve the appearance of signs of aging, including softening the appearance of deep wrinkles and creases; reducing the appearance of fine lines; and improving texture of the skin. The composition is topically administered as a lotion or cream for a period of time sufficient to accomplish the desired effect. In some embodiments the composition is administered once daily, or twice daily, and for at least about one week, at least about two weeks, at least about one month, or longer as desired.

Specifically, the skin care compositions presented herein contain a combination of agents for lifting and firming, improving texture and brightening, and soothing and anti-inflammatory agents. Preferably the formulation is paraben-free.

The formulation is provided in a cosmetically acceptable vehicle(s), which may further comprise skin soothing/conditioning agents. Accordingly, the combinations of the active ingredients of the invention are formulated as skin care cosmetic compositions that can be applied directly to the skin so as to improve the appearance of skin texture and color. The compositions may additionally provide cosmetic benefit for aging skin, spider veins, and sun damage.

According to the first aspect of the invention, there is provided a cosmetic composition comprising: *Secale cereale* (rye) seed extract; *Avena sativa* (oat) kernel extract; acetyl decapeptide-3; glaucine; aminophylline; and oligopeptide-24. The formulation may further comprise additional cosmetic agents, including dimethyl MEA (DMAE); tocopherol (Vitamin E); biotin; panthenol; dipotassium glycyrrhizate, bisabolol and hyaluronic acid.

In the second aspect of the invention, a method is provided for improving the appearance of the skin, in particular for firming and improving the appearance of the skin of the neck, the method comprising applying topically a cosmetic composition comprising: *Secale cereale* (rye) seed extract; *Avena sativa* (oat) kernel extract; acetyl decapeptide-3; glaucine; aminophylline; and oligopeptide-24. The formulation may further comprise additional cosmetic agents, including dimethyl MEA (DMAE); tocopherol (Vitamin E); biotin; panthenol; dipotassium glycyrrhizate, bisabolol and hyaluronic acid.

DETAILED DESCRIPTION OF THE EMBODIMENTS

Topical compositions are provided for improving the appearance of the skin, including the fine skin of the neck. The cosmetic formulations improve the appearance of signs of aging, including softening the appearance of deep wrinkles and creases; reducing the appearance of fine lines; and improving texture of the skin. The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders. The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

Components of the Cosmetic Compositions

*Secale cereale* (Rye) Seed Extract. Rye seed extract may be present in the composition at a concentration of from about 0.1 to 0.5%, usually about 0.15 to 0.3% by weight. *Secale cereale* (rye) seed extract is described in the art to be obtained by subjecting the aqueous solution of rye flakes to enzymatic hydrolysis. A commercially available product which comprises this rye seed extract is Coheliss® Bio (Silab, France, RM-C365). The product comprises 6 wt % rye seed extract, 93.7 wt % water and 0.3 wt % preservative (INCI: Water & *Secale cereale* (rye) seed extract).

*Avena sativa* (Oat) Kernel Extract. Oat kernel extract may be present in the composition at a concentration of from about 0.1 to 0.5%, usually about 0.15 to 0.3% by weight. A commercially available product which comprises this oat kernel extract is Osilift® (Silab, France RM0063). The product comprises 10.5% *Avena sativa* kernel extract and 88.8% water.

Glaucine ((S)-5,6,6a,7-tetrahydro-1,2,9,10-tetramethoxy-6-methyl-4H-dibenzo[de,g]quinoline, CAS Number 475-81-0) may be present in the composition at a concentration of from about 0.001 to 0.01%, usually about 0.002 to 0.005% by weight. Glaucine is available commercially, for example as a component of Bodyfit™ (Sederma).

Acetyl Decapeptide-3 may be present in the composition as a concentration of from about 0.001 to 0.01%, usually about 0.002 to 0.005% by weight. Acetyl decapeptide-3 is a growth factor mimetic. A commercially available product that comprises this decapaptide is Rejuline™ (Caregen).

Aminophylline, (CAS Number 317-34-0) is a compound of theophylline with ethylenediamine in 2:1 ratio. The aminophylline may be anhydrous. It may be present in the composition at a concentration of from about 0.1 to 5%, usually from about 0.5 to 2.5% by weight.

Dimethyl MEA (DMAE, NN-Dimethylethanolamine; CAS Number 108-01-0) may be present in the composition at a concentration of from about 0.5 to 5%, usually about 1-2.5% by weight.

Oligopeptide-24 may be present in the composition at a concentration of from about 0.0005 to 0.0005%, usually about 0.001 to 0.0025% by weight. The oligopeptide is a biomimetic. The oligopeptide is commercially available as CG-EDP3 encapsulated solution (Caregen).

Dipotassium glycyrrhizate ($\alpha$-d-Glucopyranosiduronic acid; CAS Number 68797-35-3) is an isolate from the licorice plant. It may be present in the composition at a concentration of from about 0.5 to 5%, usually about 1-2.5% by weight.

Bisabolol ((R',R')-$\alpha$,4-dimethyl-$\alpha$-(4-methyl-3-pentenyl) cyclohex-3-ene-1-methanol, CAS Number 515-69-5/23089-26-1) is a skin soothing agent, that may be present in the composition at a concentration of from about from 0.05 to 0.5%, usually about 0.1-0.25% by weight.

Tocopherol (3,4-Dihydro-2,5,7,8-tetramethyl-2-(4,8,12-trimethyltridecyl)-2H-benzopyran-6-01; Vitamin E, CAS Number 1406-66-2) is also a skin soothing agent, and may be present at a concentration of from about 0.05% to 0.5%, usually about 0.25-0.75% by weight.

Biotin is a water soluble B vitamin (5-[(3aS,4S,6aR)-2-oxohexahydro-1H-thieno[3,4-d]imidazol-4-yl]pentanoic acid; CAS Number 58-85-5) used as a skin conditioning agent. It may be present at a concentration of from about 0.00001% to 0.0001%, usually about 0.000025-0.000075% by weight.

Panthenol (CAS Number 16485-10-2) is a pro-vitamin moisturizing agent related to Vitamin E. Panthenol or panthenol derivatives (e.g., ethyl panthenol) are easily incorporated into cosmetic formulations and readily penetrate the skin. It is may present at a concentration of from about 0.05% to 0.5%, usually about 0.25-0.75% by weight.

Hyaluronic acid (CAS Number 9067-32-7) is an anionic, nonsulfated glycosaminoglycan that is a hydrating agent. It may be present at a concentration of from about 0.005 to 0.05%, usually about 0.01-0.25% by weight.

The compositions of the invention may optionally comprise other skin benefit materials. These include estradiol; progesterone; pregnanalone; coenzyme Q10; methylsolanomethane (MSM); copper peptide (copper extract); plankton extract (phytosome); kojic acid; ascorbyl palmitate; all-trans-retinol; broparoestrol; estrone; adrostenedione; androstanediols; hydroquinone; isoflavones; alpha-arbutin, etc. The steroids will generally be present at a concentration of less than about 5% or about 10% of the total by weight of the composition, while the other skin benefit materials may be present at higher levels, for example as much as about 10 to about 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen, titanium dioxide or zinc oxide may also be used. The exact amount of sunscreen employed in the compositions can vary depending upon the degree of protection desired from the sun's UV radiation.

The amounts of cosmetic or dermatological auxiliaries and additives and perfume to be used in each case can easily be determined by simple exploratory experiments by the person skilled in the art, depending on the nature of the product in question.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are crosslinked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a retinoid, a stable kojic acid derivative, and a resorcinol derivative, which may be a synergistic combination, and optionally in combination with one or more of a permeation enhancer, an azelaic acid or a derivative thereof, salicylic acid or a derivative thereof, glycolic acid or a derivative thereof, licorice extract, and green tea extract, and/or a cosmetically acceptable vehicle. Furthermore, a composition of the invention may include additional agents or additives that are not in themselves active agents but play a role in promoting the usefulness or effectiveness of an active agent.

Compositions of the invention may be applied to any subject and used to treat a variety of conditions, for example aged or sun-damaged skin of the neck, for which the compositions may provide firming, and softening of the appearance of wrinkles. A typical composition of the invention is formulated as a solution, lotion, cream, gel, ointment, liniment, solvent, emulsion, dispersion, hydrodispersion, etc., which may be applied topically to the skin so as to treat, prevent, wash, condition or otherwise effect a condition of the skin.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the neck, the hands, hands, the face, the arms, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates a topical composition according to the present invention. The composition can be processed in conventional manner and is suitable for cosmetic use. In particular the compositions are suitable for application to a site of interest for the treatment of a variety of skin conditions.

| Marini Juveneck Cream | |
| --- | --- |
| Active ingredients | concentration by weight |
| Secale Cereale (Rye) Seed Extract | 0.15 to 0.3% |

-continued

| Marini Juveneck Cream | |
|---|---|
| Active ingredients | concentration by weight |
| Avena Sativa (Oat) Kernel Extract | 0.15 to 0.3% |
| Glaucine | 0.002 to 0.005% |
| Acetyl Decapeptide-3 | 0.002 to 0.005% |
| Aminophylline | 0.5 to 2.5% |
| Dimethyl MEA (DMAE) | 1-2.5% |
| Oligopeptide-24 | 0.001 to 0.0025% |
| Dipotassium Glycyrrhizate | 1-2.5% |
| Bisabolol | 0.1-0.25% |
| Tocopherol (Vitamin E) | 0.25-0.75% |
| Biotin | 0.000025-0.000075% |
| Panthenol | 0.25-0.75% |
| Hyaluronic Acid | 0.01-0.25% |

Additional ingredients can be included to provide a cosmetically acceptable vehicle, and may comprise water, glycerin, caprylic/capric triglyceride, glyceryl stearate, *Butyrospermum parkii* (shea) butter, cetyl alcohol, dimethicone, cyclopentasiloxane, citric acid, *Prunus amygdalus dulcis* (sweet almond) oil, cyclohexasiloxane, *Glycine soja* (soybean) oil, sodium stearoyl glutamate, squalane, aluminum starch octenylsuccinate, pentylene glycol, sodium oleate, hydrogenated lecithin, ethyl alcohol, coco-glucoside, caprylyl glycol, sodium citrate, ethylhexylglycerin, hexylene glycol, acrylates/c10-30 alkyl acrylate crosspolymer, xanthan gum, triethanolamine, disodium edta, phenoxyethanol.

In a clinical study report, 71 subjects tested the Juveneck cream, applied to the neck twice daily for a period of three months. When compared to baseline, over 94% of subjects reported improved texture with smoother, softer skin; and liked the product and results.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application comprising:
  from 0.1 to 0.5% by weight *Secale cereale* (rye) seed extract; from 0.1 to 0.5% by weight *Avena sativa* (oat) kernel extract; from 0.001 to 0.01% by weight acetyl decapeptide-3; from 0.001 to 0.01% by weight glaucine; from 0.1 to 5% by weight aminophylline; and from 0.0005 to 0.005% by weight oligopeptide-24; and
  a cosmetically acceptable vehicle.

2. The composition of claim 1, further comprising from 0.5 to 5% by weight NN-dimethylethanolamine (DMEA).

3. The composition of claim 1, further comprising from 0.5 to 5% by weight dipotassium glycyrrhizate.

4. The composition of claim 1, further comprising from 0.05 to 0.5% by weight bisabolol.

5. The composition of claim 1, further comprising from 0.05% to 0.5% by weight tocopherol.

6. The composition of claim 1, further comprising from 0.00001% to 0.0001% by weight biotin.

7. The composition of claim 1, further comprising from 0.05% to 0.5% by weight panthenol.

8. The composition of claim 1, further comprising from 0.005 to 0.05% by weight hyaluronic acid.

9. The composition of claim 1, comprising by weight:
  0.15 to 0.3% *Secale cereale* (rye) seed extract; 0.15 to 0.3% *Avena sativa* (oat) kernel extract; 0.002 to 0.005% glaucine; 0.002 to 0.005% acetyl decapeptide-3; 0.5 to 2.5% aminophylline; 1-2.5% DMAE; 0.001 to 0.0025% oligopeptide-24; 1-2.5% dipotassium glycyrrhizate; 0.1-0.25% bisabolol; 0.25-0.75% tocopherol; 0.000025-0.000075% biotin; 0.25-0.75% panthenol; 0.01-0.25% hyaluronic acid; and
  a cosmetically acceptable vehicle.

10. The composition of claim 9, wherein the cosmetically acceptable vehicle is a cream.

11. A method of improving the appearance of aged or sun-damaged skin, comprising:
  topically applying a cosmetic composition comprising:
    from 0.1 to 0.5% by weight *Secale cereale* (rye) seed extract; from 0.1 to 0.5% by weight *Avena sativa* (oat) kernel extract; from 0.001 to 0.01% by weight acetyl decapeptide-3; from 0.001 to 0.01% by weight glaucine; from 0.1 to 5% by weight aminophylline; and from 0.0005 to 0.005% by weight oligopeptide-24; and
    a cosmetically acceptable vehicle.

12. The method of claim 11, wherein the cosmetic composition further comprises from 0.5 to 5% by weight NN-dimethylethanolamine (DMAE).

13. The composition of claim 11, further comprising from 0.5 to 5% by weight dipotassium glycyrrhizate.

14. The method of claim 11, wherein the cosmetic composition further comprises from 0.05 to 0.5% by weight bisabolol.

15. The method of claim 11, wherein the cosmetic composition further comprises from 0.05% to 0.5% by weight tocopherol.

16. The method of claim 11, wherein the cosmetic composition further comprises from 0.00001% to 0.0001% by weight biotin.

17. The method of claim 11, wherein the cosmetic composition further comprises from 0.05% to 0.5% by weight panthenol.

18. The method of claim 11, wherein the cosmetic composition further comprises from 0.005 to 0.05% by weight hyaluronic acid.

19. The method of claim 11, wherein the cosmetic composition comprises:
  0.15 to 0.3% *Secale cereale* (rye) seed extract; 0.15 to 0.3% *Avena sativa* (oat) kernel extract; 0.002 to 0.005% glaucine; 0.002 to 0.005% acetyl decapeptide-3; 0.5 to 2.5% aminophylline; 1-2.5% DMAE; 0.001 to 0.0025% oligopeptide-24; 1-2.5% dipotassium glycyrrhizate; 0.1-0.25% bisabolol; 0.25-0.75% tocopherol; 0.000025-0.000075% biotin; 0.25-0.75% panthenol; 0.01-0.25% hyaluronic acid; and
  a cosmetically acceptable vehicle.

20. The method of claim 19, wherein the cosmetic composition is applied to the neck.

* * * * *